(12) United States Patent
Sheu et al.

(10) Patent No.: US 11,903,907 B2
(45) Date of Patent: Feb. 20, 2024

(54) SOLUBLE HONOKIOL DERIVATIVES

(71) Applicants: TAIPEI MEDICAL UNIVERSITY, Taipei (TW); CATHAY GENERAL HOSPITAL, Taipei (TW)

(72) Inventors: Joen-Rong Sheu, Taipei (TW); Fa-Kung Lee, Taipei (TW); Chih-Cheng Chien, Taipei (TW); Chih-Ming Ho, Taipei (TW); Chao-Chien Chang, Taipei (TW); Cheng-Ying Hsieh, New Taipei (TW); Jing-Ping Liou, Taipei (TW)

(73) Assignees: TAIPEI MEDICAL UNIVERSITY, Taipei (TW); CATHAY GENERAL HOSPITAL, Taipei (TW)

( * ) Notice: Subject to any disclaimer, the term of this patent is extended or adjusted under 35 U.S.C. 154(b) by 260 days.

(21) Appl. No.: 16/931,959

(22) Filed: Jul. 17, 2020

(65) Prior Publication Data
US 2020/0358554 A1    Nov. 12, 2020

Related U.S. Application Data

(62) Division of application No. 16/169,322, filed on Oct. 24, 2018, now abandoned.

(60) Provisional application No. 62/576,464, filed on Oct. 24, 2017.

(51) Int. Cl.
| | |
|---|---|
| *A61K 31/05* | (2006.01) |
| *H04L 27/20* | (2006.01) |
| *A61P 25/00* | (2006.01) |
| *A61K 9/00* | (2006.01) |
| *H03M 13/11* | (2006.01) |
| *H03M 13/25* | (2006.01) |
| *H03M 13/27* | (2006.01) |
| *H03M 13/37* | (2006.01) |
| *H03M 13/00* | (2006.01) |
| *H04L 1/00* | (2006.01) |
| *H03M 13/15* | (2006.01) |

(52) U.S. Cl.
CPC ........... *A61K 31/05* (2013.01); *A61K 9/0019* (2013.01); *A61P 25/00* (2018.01); *H03M 13/1165* (2013.01); *H03M 13/255* (2013.01); *H03M 13/2707* (2013.01); *H03M 13/2778* (2013.01); *H03M 13/3761* (2013.01); *H03M 13/3769* (2013.01); *H03M 13/6356* (2013.01); *H03M 13/6362* (2013.01); *H04L 1/0041* (2013.01); *H04L 1/0045* (2013.01); *H04L 1/0057* (2013.01); *H04L 1/0065* (2013.01); *H04L 1/0067* (2013.01); *H04L 1/0071* (2013.01); *H03M 13/152* (2013.01); *H04L 27/20* (2013.01)

(58) Field of Classification Search
CPC ....... A61K 31/05; A61K 9/0019; A61P 25/00; H03M 13/1165; H03M 13/255; H03M 13/2707; H03M 13/2778; H03M 13/3761; H03M 13/3769; H03M 13/6356; H03M 13/6362; H03M 13/152; H04L 1/0041; H04L 1/0045; H04L 1/0057; H04L 1/0065; H04L 1/0067; H04L 1/0071; H04L 27/20
See application file for complete search history.

(56) References Cited

FOREIGN PATENT DOCUMENTS

CN    107098832    *    8/2017

OTHER PUBLICATIONS

CN107098832-machine-translation, 2022, machine translation of description of CN107098832.*

* cited by examiner

*Primary Examiner* — Sun Jae Yoo
(74) *Attorney, Agent, or Firm* — WPAT, PC

(57) ABSTRACT

The invention provides a soluble honokiol derivative (such as a water soluble honokiol derivative) and its application in antagonizing glycoprotein VI receptor and providing antioxidant and neuroprotective effects.

18 Claims, 6 Drawing Sheets

| Parameters | HP-TMU (0.5 mg/kg) |
|---|---|
| $t_{1/2}$ (min) | 27.13 ± 8.34 |
| $C_0$ (ng/mL) | 8613.11 ± 2412.35 |
| AUC (min*ng/mL) | 175395.5 ± 68603.6 |
| Cl (mL/min/kg) | 274.81 ± 89.04 |
| $V_{ss}$ (L/kg) | 16.88 ± 3.56 |

SOLUBLE HONOKIOL DERIVATIVES

FIELD OF THE INVENTION

The present invention is related to the field of compounds, compositions and methods for treatment or prevention. Particularly, the invention provides a soluble honokiol derivative (such as a water soluble honokiol derivative) and its application in antagonizing glycoprotein VI receptor and providing antioxidant and neuroprotective effects.

BACKGROUND OF THE INVENTION

Stroke is a medical condition in which the brain's blood vessels are clogged or broken, leading to brain cell ischemia or death or injury. World Health Organization data shows that stroke is the second most frequent cause of death and each year about 6.0 million deaths resulted from stroke. Stroke can be divided into two types, namely, hemorrhagic stroke and ischemic stroke (about 80% of all stroke cases) which causes cerebral vascular thrombosis.

Honokiol obtained from the stem of *Magnolia officinalis* was reported to have effects in improving brain damage caused by ischemic stroke and a potent antioxidant and neuroprotective effects. CN 103113264 discloses a magnolol derivative, a honokiol derivative and preparation method and application thereof. However, due to poor solubility in water or oil for honokiol, it is not suitable for clinical use in the treatment of ischemic stroke.

SUMMARY OF THE INVENTION

The present disclosure provides a compound having Formula (I) as disclosed herein. Certain embodiments include the compounds wherein $R_1$ is phosphate; $R_2$ and $R_3$ are each independently $C_{2-6}$alkenyl; and $R_4$ and $R_5$ are each independently H; or a pharmaceutically acceptable salt thereof. Some embodiments, $R_2$ and $R_3$ are each independently ethenyl; or a pharmaceutically acceptable salt thereof. In one embodiment, the pharmaceutically acceptable salt is a sodium salt. Particular embodiments of the compound can be 3',5-diallyl-[1,1'-biphenyl]-2,4'-diyl bis(phosphate) or sodium 3',5-diallyl-[1,1'-biphenyl]-2,4'-diyl bis(phosphate).

The present disclosure also provides a pharmaceutical composition, which comprises a therapeutically effective amount of a compound of Formula (I) and optionally one or more pharmaceutically acceptable carriers and/or excipients. In one embodiment, the pharmaceutical composition is in a dosage form.

The present disclosure also provides a method of antagonizing glycoprotein VI receptor, comprising administration of a therapeutically effective amount of a compound of the present disclosure to a subject. In one embodiment, platelet aggregation can be inhibited by the method.

The present disclosure also provides a method of providing antioxidant and neuroprotective effects in a subject, comprising administering a therapeutically effective amount of a compound of the present disclosure to the subject. Certain embodiments of the method include that the method reduces edema and does not cause hemorrhage. In the methods described herein, the compound has a prolonged half-life compared to honokiol and/or converts to honokiol in plasma.

In one embodiment, the neuroprotective effect diminishes brain damage in the subject. In a further embodiment, the brain damage is ischemic stroke.

In one embodiment, the administration is parenteral administration. In a further embodiment, the parenteral administration is intravenous, intramuscular or intracranial administration.

BRIEF DESCRIPTION OF THE DRAWING

FIG. 4A and FIG. 4B show the A. mean plasma concentrations of honokiol vs. time profile in five rats after intravenous injection of HP-TMU(●) or honokiol(■); and B. pharmacokinetic parameters of HP-TMU in rat plasma.

DETAILED DESCRIPTION OF THE INVENTION

Figure 1:
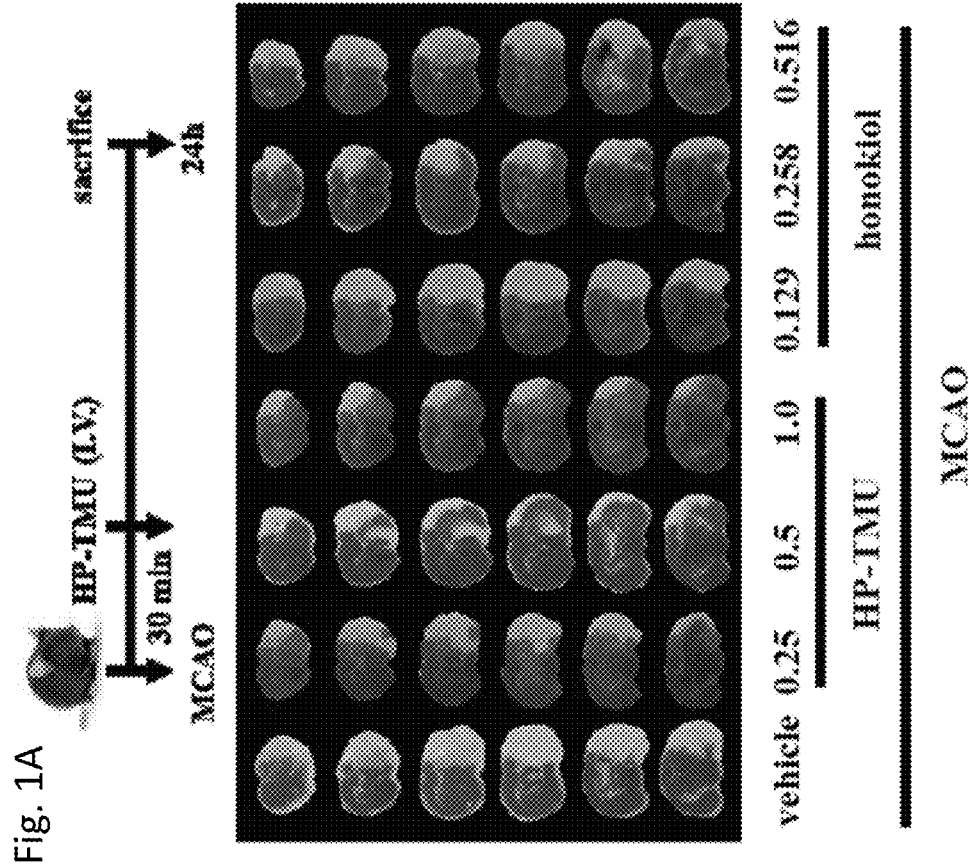
FIG. 1A shows coronal sections of 2,3,5-triphenyltetrazolium chloride (TTC)-stained brains after middle cerebral artery occlusion (MCAO) in the vehicle group treated with an isovolumetric solvent (normal saline, intravenous [i.v.]), and groups treated with HP-TMU (0.25, 0.5 and 1 mg/kg, i.v.) or honokiol (0.129, 0.258 and 0.516 mg/kg, i.v.; the doses of honokiol were adjusted by the ratio of the molecular weight of honokiol to HP-TMU (266.33/514.22)) after 30 min-embolic occlusion. The densitometric analyses for the measurement of infarct volume and brain edema after treatment with HP-TMU or honokiol against embolic stroke in mice were shown in FIG. 1B & FIG. 1C, respectively. Data are presented as the means±SEM (n=8). *$P<0.05$ compared with the vehicle group.

In accordance with the present disclosure and as used herein, the following terms are defined with the following meanings, unless explicitly stated otherwise. It is to be understood that both the foregoing general description and the following detailed description are examples and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, the singular forms "a," "an" and "the" include plural referents unless the context clearly dictates otherwise.

As used herein, the term "prodrug" refers to a compound (e.g., a drug precursor) that is transformed in vivo to yield a parent compound or a pharmaceutically acceptable salt, hydrate or solvate of the parent compound.

As used herein, the term "alkyl" refers to a saturated straight or branched hydrocarbon, such as a straight or branched group of 1-6, 1-4, or 1-3 carbon atoms, referred to herein as $C_1$-$C_6$alkyl, $C_1$-$C_4$alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

As used herein, the terms "halo" or "halogen" as used herein refer to F, Cl, Br, or I.

As used herein, the term "alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

As used herein, the term "pharmaceutically acceptable" means approved or approvable by a regulatory agency of the Federal government of the United States of America or the corresponding agency in countries other than the United States of America (such as the EMA, the European Medicines Agency), or that is listed in the United States Pharmacopeia or European Pharmacopoeia (Ph. Eur.).

As used herein, the term "bioavailable" is art-recognized and refers to a form of the subject disclosure that allows for it, or a portion of the amount administered, to be absorbed by, incorporated to, or otherwise physiologically available to a subject or patient to whom it is administered.

As used herein, the terms "treating" or "treatment" of a disease includes inhibiting the disease (slowing or arresting or partially arresting its development), preventing the disease, providing relief from the symptoms or side effects of the disease (including palliative treatment), and/or relieving the disease (causing regression of the disease.

As used herein, a "patient," "subject" or "host" to be treated by the subject method may mean either a human or non-human animal. Non-human animals include companion animals (e.g. cats, dogs) and animals raised for consumption (i.e. food animals), such as cows, pigs, chickens.

As used herein, the term "neuroprotection" refers to the prevention or inhibition of degenerative effects of injury or disease in the NS, including protection from the secondary neurodegenerative effects which persist even when the primary risk factor is removed or attenuated.

The present disclosure provides a novel honokiol derivative with enhanced stability and surprisingly good bioavailability. Particularly, the compound of the present invention can be used to prepare parenteral or injectable drug delivery.

In one aspect, the present disclosure provides a compound having the following formula:

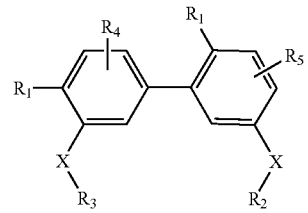

(I)

wherein

X is $(CH_2)_{1-6}$;

$R_1$ is phosphate or carbonate;

$R_2$ and $R_3$ are each independently $C_{2-6}$alkenyl, $C_{1-10}$alkyl, —O—$C_{1-10}$alkyl or —NH—$C_{1-10}$alkyl, wherein the alkyl or alkenyl is unsubstituted or substituted;

$R_4$ and $R_5$ are each independently one to three H, halogen, —OH, —$NH_2$, $NO_2$, $C_{1-10}$alkyl, $C_{2-6}$alkenyl, —O—$C_{1-10}$alkyl or —NH—$C_{1-10}$alkyl;

or a pharmaceutically acceptable salt thereof.

In one embodiment, $R_1$ is phosphate; $R_2$ and $R_3$ are each independently $C_{2-6}$alkenyl; and $R_4$ and $R_5$ are each independently H. In a further embodiment, $R_2$ and $R_3$ are each independently ethenyl.

The pharmaceutically acceptable salts as used herein refer to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. In one embodiment, the pharmaceutically acceptable salt is a sodium salt.

In one embodiment, the compound of the present invention is 3',5-diallyl-[1,1'-biphenyl]-2,4'-diylbis(phosphate) or sodium 3',5-diallyl-[1,1'-biphenyl]-2,4'-diylbis(phosphate).

The present disclosure provides a preparation method of a honokiol derivative represented by formula (I). The synthetic procedure for honokiol phosphate (3) is illustrated in the following scheme 1. Honokiol (Compound 1) as a starting substance was reacted with dibenzyl phosphite in the presence of N-chlorosuccinimide to afford compound 2. The benzyl groups of the resulting product were removed using bromotrimethylsilane followed by basification by sodium methoxide to obtain the corresponding phosphate 3.

Scheme 1

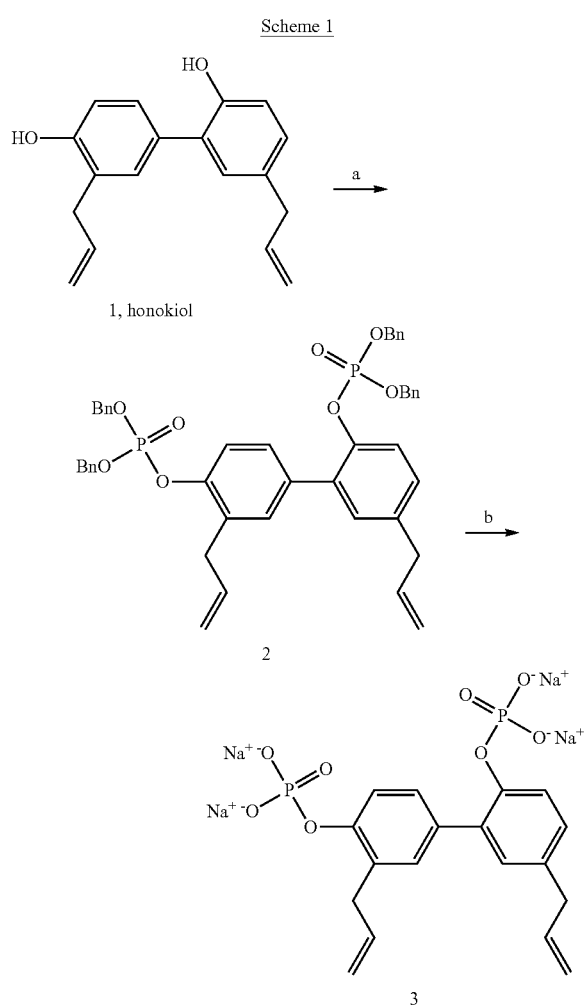

Reagents and conditions: (a) N-chlorosuccinimide, dibenzyl phosphite, DMAP, DIEA, acetonitrile; (b) i. bromotrimethylsilane, CH$_2$Cl$_2$; ii. sodium methoxide, EtOH.

In order to use the compound of Formula (I) in therapy, it will normally be formulated into a pharmaceutical composition in accordance with standard pharmaceutical practice.

The present disclosure therefore provides a pharmaceutical composition, which comprises a therapeutically effective amount of a compound of Formula (I) and optionally one or more pharmaceutically acceptable carriers and/or excipients.

The present disclosure also provides a dosage form comprising the pharmaceutical composition of the invention. In one embodiment, the dosage form is an injection dosage form.

A pharmaceutical composition of the invention, which may be prepared by admixture, suitably at ambient temperature and atmospheric pressure, is usually adapted for oral administration and, as such, may be in the form of tablets, capsules, oral liquid preparations, powders, granules, or lozenges.

Compositions containing the active ingredient may be in any form suitable for the intended method of administration. In some embodiments, the compounds of a method and/or composition described herein can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

The terms "parenteral administration" and "administered parenterally" are art-recognized and refer to modes of administration other than enteral and topical administration, usually by injection, and includes, without limitation, intravenous, intramuscular, intracranial, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion. For example, Formulations suitable for parenteral administration include aqueous and non-aqueous isotonic sterile injection solutions which may contain, for example, antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

When the compounds are administered via oral administration, for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments unit dosage formulations contain a daily dose or unit, daily sub-dose, or an appropriate fraction thereof, of a drug. In one embodiment, the unit dosage formulation is an injection dosage form. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

In a further aspect there is provided a method of antagonizing glycoprotein VI receptor, comprising administration of a therapeutically effective amount of the compound of Formula (I) to the subject. In one embodiment, the compound can inhibit platelet aggregation.

Glycoprotein (GP) VI is a platelet membrane protein with a molecular weight of 62 kDa that was identified as a physiological collagen receptor from studies of patients deficient in this protein. GPVI-deficient platelets lacked specifically collagen-induced aggregation and the ability to form thrombi on a collagen surface under flow conditions, suggesting that GPVI makes an indispensable contribution to collagen-induced platelet activation.

The present invention also provides a method of providing antioxidant and neuroprotective effects in a subject, comprising administering a therapeutically effective amount of the compound of Formula (I) to the subject.

The present disclosure also provides a method of improving brain damage in a subject, which comprises administration of a therapeutically effective amount of the compound of Formula (I) to the subject. In one embodiment, the brain damage is ischemic stroke.

In one embodiment, the methods described herein do not cause hemorrhage.

In one embodiment, the methods described herein reduces edema.

In the methods described herein, the compound of the present disclosure has a prolonged half-life compared to honokiol.

In the methods described herein, the compound of the present disclosure converts to honokiol in plasma.

The dose range of the compounds of general formula (I) applicable per day is usually from about 0.01 to about 1.0 mg per kg body weight, preferably from about 0.025 to about 1.0, about 0.05 to about 1.0, about 0.075 to about 1.0, about 0.025 to about 0.1, about 0.05 to about 0.1, about 0.75 to about 0.1, about 0.1 to about 1.0, about 0.25 to about 1.0, about 0.5 to about 1.0 or about 0.75 to about 1.0 mg per kg body weight of the patient.

The examples which follow are intended in no way to limit the scope of the disclosure but are provided to illustrate how to prepare and use compounds disclosed herein. Many other embodiments of this disclosure will be apparent to one skilled in the art.

EXAMPLE

Example 1 Preparation of Tetrabenzyl (3',5-diallyl-[1,1'-biphenyl]-2,4'-diyl) bis(phosphate) (2) (HP-TMU)

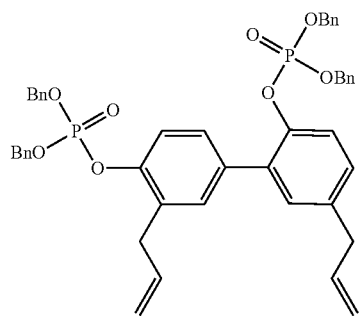 [SMILES: C=CCc1ccc(OP(=O)(OCc2ccccc2)OCc2ccccc2)c(-c2ccc(OP(=O)(OCc3ccccc3)OCc3ccccc3)c(CC=C)c2)c1]

A solution of N-chlorosuccinimide (5.0 equiv) in $CH_3CN$ was heated at 40° C. for 5 min. A solution of dibenzyl phosphite (5.0 equiv) in $CH_3CN$ was added to this prepared solution and stirred at room temperature for 4 hours. Meanwhile, a solution of honokiol (1, 1 equiv), N,N-diisopropylethylamine (DIPEA, 5.0 equiv), and 4-dimethylaminopyridine (DMAP, 0.2 equiv) in $CH_3CN$ was prepared and added to the stirring mixture at room temperature. The resulting mixture was stirred at room temperature for 1 hour. The reaction mixture was quenched by $H_2O$ and extracted with toluene. The organic layer was collected and dried to afford tetrabenzyl (3',5-diallyl-[1,1'-biphenyl]-2,4'-diyl) bis(phosphate) (referred as compound 2).

Example 2 Preparation of Sodium 3',5-diallyl-[1,1'-biphenyl]-2,4'-diyl bis(phosphate) (3)

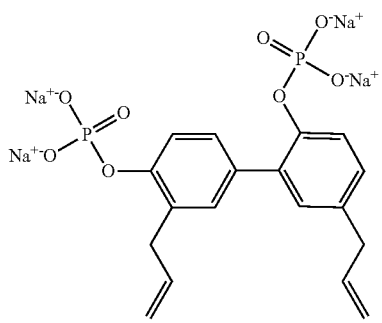

Bromotrimethylsilane was added to a solution of compound 2 (1 equiv) in $CH_2Cl_2$ was added bromotrimethylsilane under ice bath and stirred at room temperature for 3 hours. The reaction mixture was quenched by $H_2O$ and extracted with ethyl acetate. The aqueous layer was collected and dried to afford a crude product. The resulting residue was dissolved in EtOH and then sodium methoxide (4.4 equiv) was added. After stirring at room temperature for 18 hours, the organic solvent was removed in vacuum. The resulting residue was dissolved in $H_2O$ and extracted with ethyl acetate. The aqueous layer was collected and dried to afford sodium 3',5-diallyl-[1,1'-biphenyl]-2,4'-diyl bis(phosphate) (referred to as compound 3).

Example 3 HP-TMU Exerts (1) Superior Neuroprotective Effects Against Embolic Stroke as Compared to Honokiol (2) without Causing the Risk of Hemorrhagic Incidence in Mice Coronal sections of 2,3,5-triphenyltetrazolium chloride (TTC)-stained brains were taken after middle cerebral artery occlusion (MCAO) in the vehicle group treated with an isovolumetric solvent (normal saline, intravenous [i.v.]), and groups treated with HP-TMU (0.25, 0.5 and 1 mg/kg, i.v.) or honokiol (0.129, 0.258 and 0.516 mg/kg, i.v.; the doses of honokiol were adjusted by the ratio of the molecular weight of honokiol to HP-TMU (266.33/514.22)) after 30 min-embolic occlusion. The densitometric analyses for the measurement of infarct volume and brain edema were performed after treatment with HP-TMU or honokiol against embolic stroke in mice. Bleeding time was measured 10 min after the i.v. administration of normal saline (isovolumetric control) or HP-TMU (0.5 and 1 mg/kg, i.v.) for 30 min.

Figure 2:
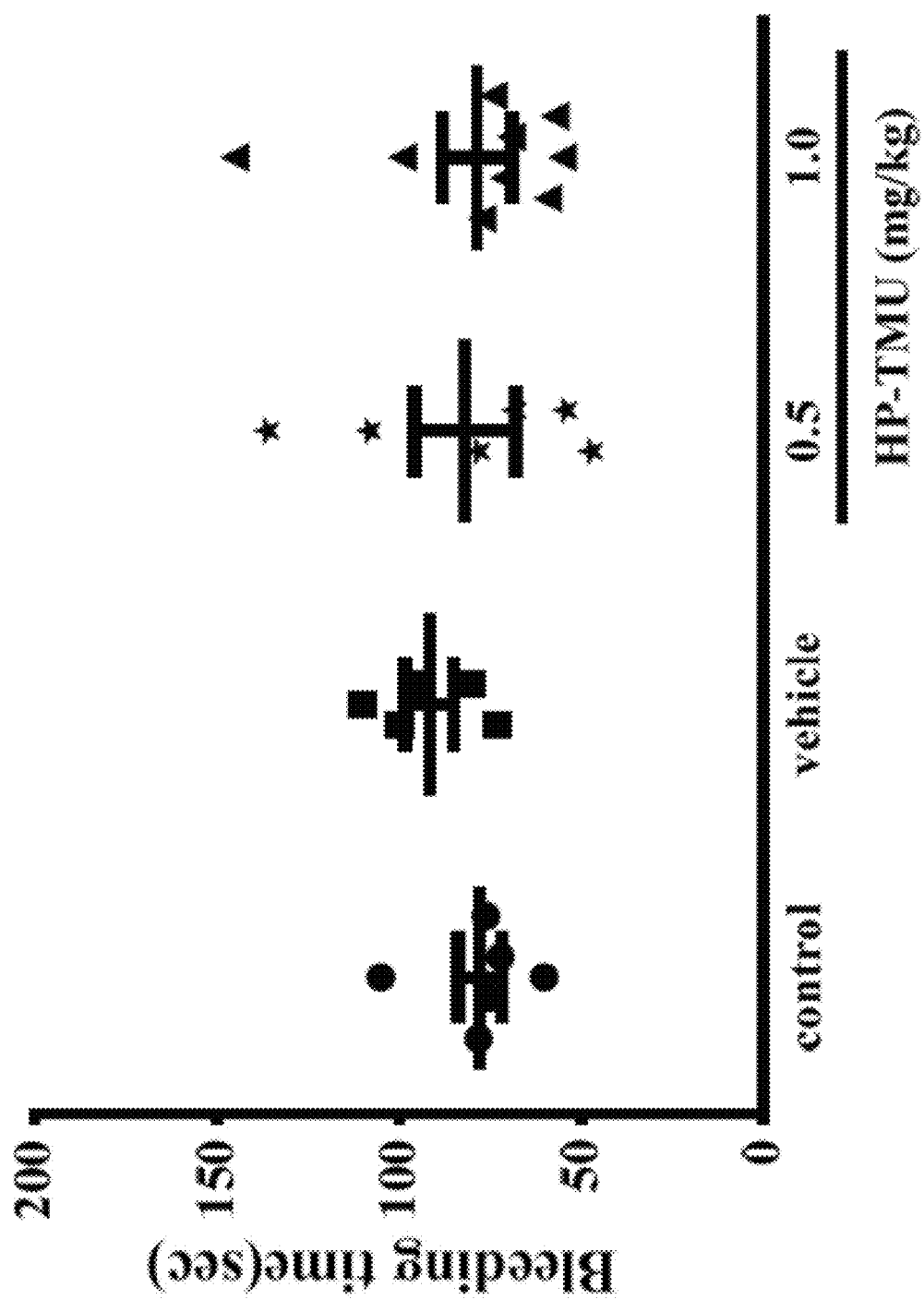
FIG. 2 shows bleeding time measured at 10 min after the i.v. administration of normal saline (isovolumetric control) or HP-TMU (0.5 and 1 mg/kg, i.v.) for 30 min. Data are presented as the means±SEM (n=6). Each symbol represents the bleeding time of an individual mouse.

As shown in FIG. 1A, the red region in the TTC-stained sections indicates the nonischemic portion of the brain, whereas the pale region indicates the ischemic portion. Treatment with HP-TMU (0.5 and 1 mg/kg) significantly reduced the infarct volume compared with that in the solvent control group (P<0.05) (FIG. 1B). In addition, MCAO-induced cerebral edema in the ischemic hemisphere was reduced by the treatment of 1 mg/kg HP-TMU (FIG. 1C). Furthermore, the administration of HP-TMU reveals more potent neuroprotective effects than honokiol in mice subjected to MCAO (FIGS. 1A-1C). On the other hand, increased risk of hemorrhage is a major side effect of anti-stroke treatments. To evaluate HP-TMU in this aspect, we used the mouse tail transection model as an index of hemostasis. As shown in FIG. 2, HP-TMU (0.5 and 1 mg/kg) did not alter the bleeding time substantially, illustrating that HP-TMU treatment for embolic stroke is harmless, eliciting no side effects of bleeding.

Example 4 HP-TMU Improves Neurobehavioral Functions in Mice after MCAO

Mice were subjected to middle cerebral artery occlusion (MCAO) surgery for 30 min, and then treated with the isovolumetric vehicle control (normal saline, intravenous [i.v.]) or HP-TMU (0.25, 0.5 and 1 mg/kg, i.v.) or honokiol (0.129, 0.258 and 0.516 mg/kg, i.v.). Assays of neurobehavioral functions include neurological severity scoring and the rotarod test. Evaluations were performed before and 24 and 48 h after surgery.

Figure 3A:
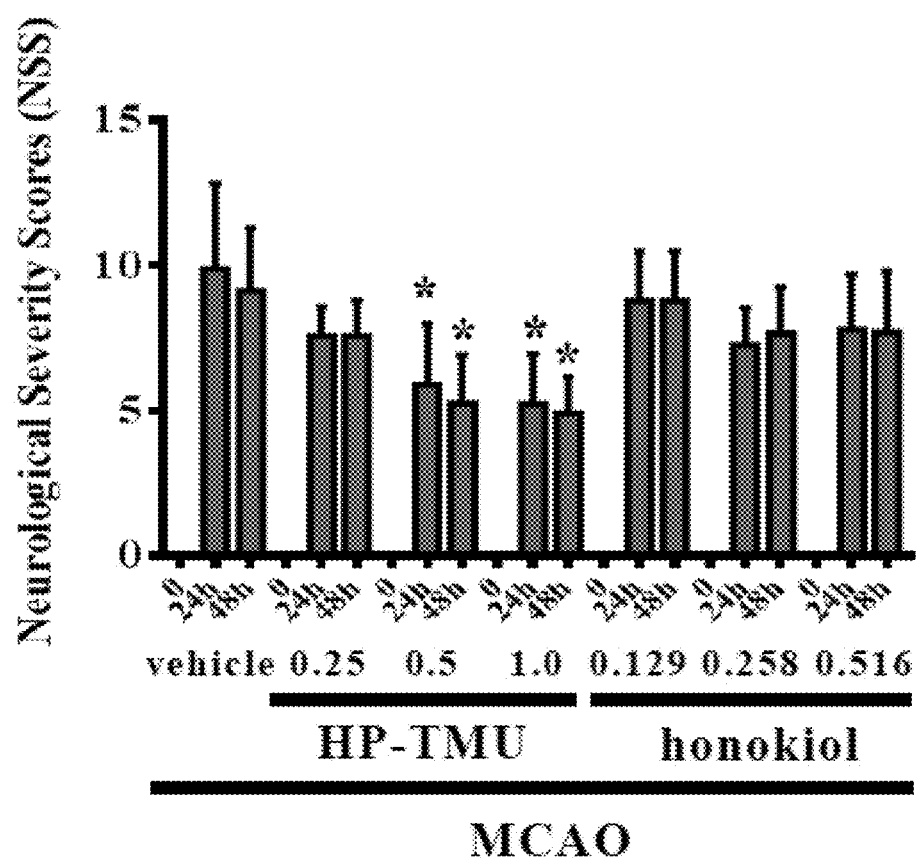
FIG. 3A and FIG. 3B show assays of neurobehavioral functions including A. neurological severity scoring and B. the rotarod test, evaluations were performed before and 24 and 48 h after surgery. All data are presented as the means±SEM (n=8). *$P<0.05$, compared with the vehicle group.
Figure 3B:
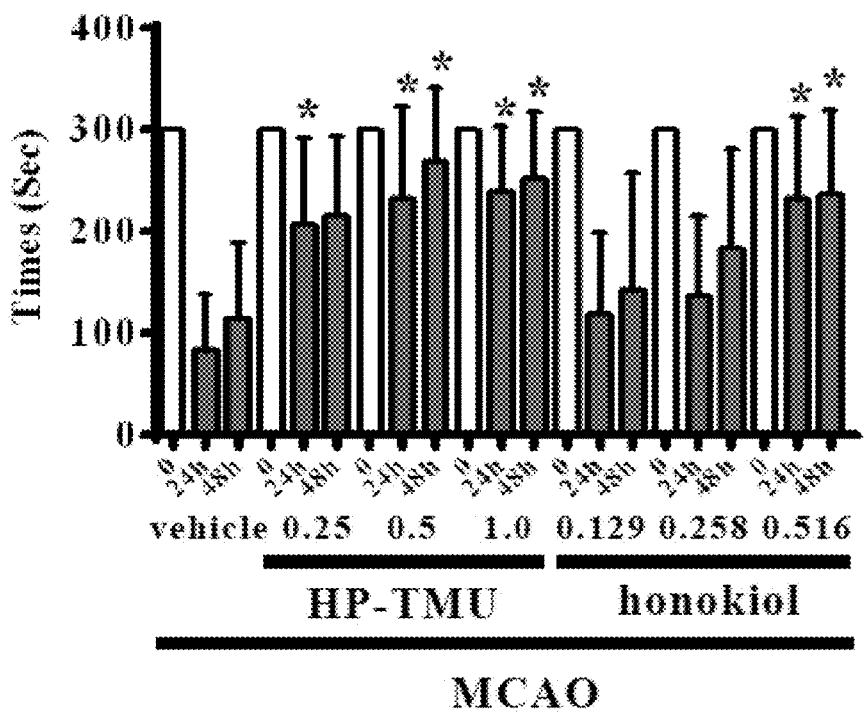

Neurological deficit was examined and scored on an 18-point scale before and 24 and 48 h after MCAO reperfusion injury. The changes in neurological deficit scores of different groups are illustrated in FIG. 3A. At 24 and 48 h after MCAO, neurobehavioral deficit scores significantly increased compared with those before MCAO; nevertheless, 0.5 and 1 mg/kg HP-TMU significantly ameliorated these increased scores (Post-24 h groups: P<0.05; Post-48 h groups: P<0.05). In addition, the performance of the MCAO group mice in the rotarod test at 24 and 48 h after MCAO was also impaired, and the decrease of rotarod duration was significant reversed in the HP-TMU (0.5 and 1 mg/kg)-treated mice compared with the vehicle control group (Post-24 h groups: P<0.05; Post-48 h groups: P<0.05) (FIG. 3B). Mean plasma concentrations of honokiol vs. time profile in five rats were measured after intravenous injection of HP-TMU or honokiol.

Figure 4A:
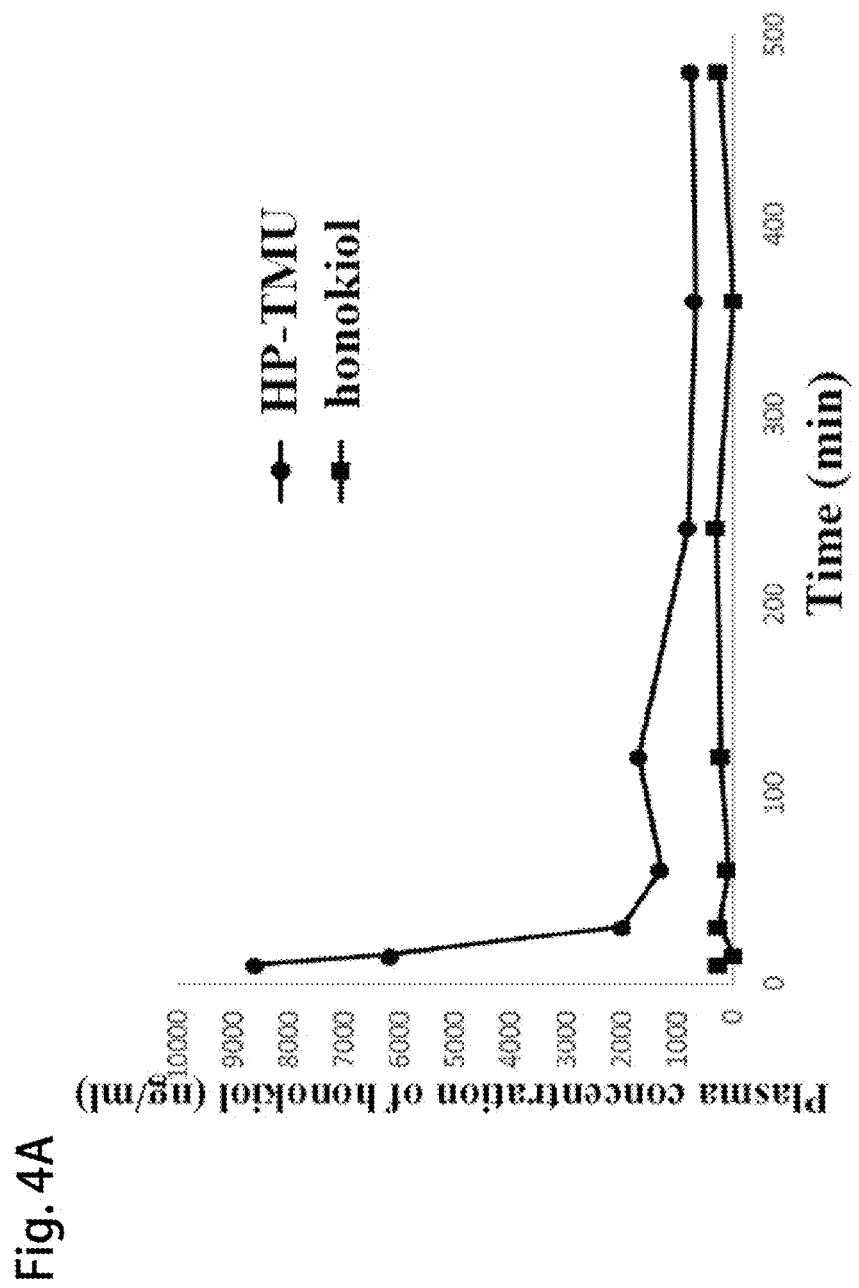

The plasma concentrations of honokiol at different points are expressed as mean±SD, and the mean concentration-time curve is shown in FIG. 4A. The calculated pharmacokinetic parameters of HP-TMU are summarized in FIG. 4B. The results revealed that intravenous administration of honokiol (0.258 mg/kg) rapidly distributed and could not be detected in plasma. However, the same dosage of HP-TMU (0.5 mg/kg) could be hydrolyzed to honokiol and be detected in rat plasma. HP-TMU has prolonged half-life compared to honokiol, and it was indeed converted to honokiol in plasma.

Example 5 Comparison of the Neuroprotective Effect of HP-TMU and Edaravone in Mice Subjected to MCAO Mice were subjected to middle cerebral artery occlusion (MCAO) surgery for 30 min, and then treated with the isovolumetric vehicle control (normal saline, intravenous [i.v.]) or HP-TMU (1 mg/kg, i.v.) or edaravone (3 mg/kg, i.v.). The therapeutic effects of HP-TMU on long-term recovery were evaluated by neurological severity scoring before or 1, 2, 7, 14, and 28 days after surgery.

Figure 5:
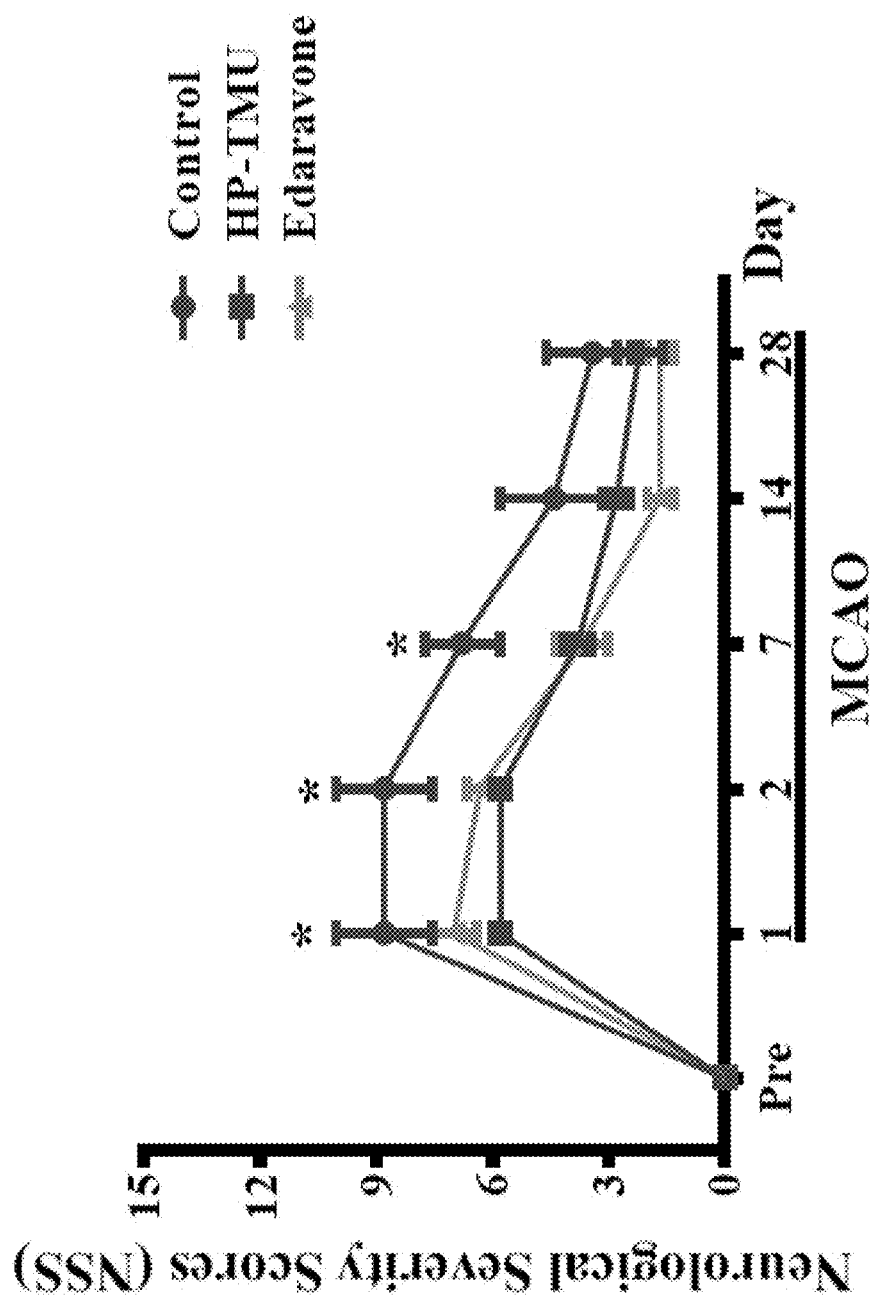
FIG. 5 shows that mice were subjected to middle cerebral artery occlusion (MCAO) surgery for 30 min, and then treated with the isovolumetric vehicle control (normal saline, intravenous [i.v.]) or HP-TMU (1 mg/kg, i.v.) or edaravone (3 mg/kg, i.v.). The therapeutic effects of HP-TMU on long-term recovery were evaluated by neurological severity scoring before or 1, 2, 7, 14, and 28 days after surgery. All data are presented as the means±SEM (n=3). *$P<0.05$, compared with the vehicle control group.

The long-term recovery of neurological deficit of MCAO mice were significantly improved by the treatment of HP-TMU (1 mg/kg) at 1, 2, and 7 days after surgery (FIG. 5). In addition, the administration of HP-TMU (1 mg/kg) reveals similar therapeutic effects compared with edaravone (3 mg/kg), an approved drug in Japan to treat acute ischemic stroke (FIG. 5).

What is claimed is:

1. A method of antagonizing glycoprotein VI receptor, comprising administration of a therapeutically effective amount of the following compound of Formula (I) to a subject:

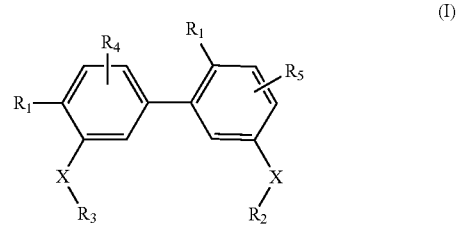

(I)

wherein

X is $(CH_2)_{1-6}$;

$R_1$ is phosphate or carbonate;

$R_2$ and $R_3$ are each independently $C_{2-6}$alkenyl, $C_{1-10}$alkyl, —O—$C_{1-10}$alkyl or —NH—$C_{1-10}$alkyl, wherein the alkyl or alkenyl is unsubstituted or substituted; and $R_4$ and $R_5$ are each independently one to three H, halogen, —OH, —$NH_2$, $NO_2$, $C_{1-10}$alkyl, $C_{2-6}$alkenyl, —O—$C_{1-10}$alkyl or —NH—$C_{1-10}$alkyl;

or a pharmaceutically acceptable salt thereof;

wherein the compound or a pharmaceutically acceptable salt thereof is administered by intravenous injection; and wherein the compound or a pharmaceutically acceptable salt thereof is administered at a dose of about 0.01 to about 1.0 mg per kg body weight.

2. The method of claim 1, wherein $R_1$ is phosphate; $R_2$ and $R_3$ are each independently $C_{2-6}$alkenyl; and $R_4$ and $R_5$ are each independently H; or a pharmaceutically acceptable salt thereof.

3. The method of claim 1, wherein $R_2$ and $R_3$ are each independently ethenyl; or a pharmaceutically acceptable salt thereof.

4. The method of claim 1, wherein the pharmaceutically acceptable salt is a sodium salt.

5. The method of claim 1, wherein the compound is 3',5-diallyl-[1,1'-biphenyl]-2,4'-diyl bis(phosphate), or a pharmaceutically acceptable salt thereof.

6. The method of claim 1, wherein the compound is sodium 3',5-diallyl-[1,1'-biphenyl]-2,4'-diylbis(phosphate).

7. The method of claim 1, wherein platelet aggregation can be inhibited in the subject.

8. A method of providing antioxidant and neuroprotective effects in a subject, comprising administering a therapeutically effective amount of a compound of Formula (I) to a subject:

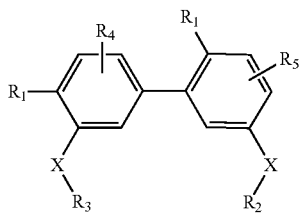

(I)

wherein
X is $(CH_2)_{1-6}$;
$R_1$ is phosphate or carbonate;
$R_2$ and $R_3$ are each independently $C_{2-6}$alkenyl, $C_{1-10}$alkyl, —O—$C_{1-10}$alkyl or —NH—$C_{1-10}$alkyl, wherein the alkyl or alkenyl is unsubstituted or substituted; and
$R_4$ and $R_5$ are each independently one to three H, halogen, —OH, —$NH_2$, $NO_2$, $C_{1-10}$alkyl, $C_{2-6}$alkenyl, —O—$C_{1-10}$alkyl or —NH—$C_{1-10}$alkyl;
or a pharmaceutically acceptable salt thereof;
wherein the compound or a pharmaceutically acceptable salt thereof is administered by intravenous injection; and
wherein the compound or a pharmaceutically acceptable salt thereof is administered at a dose of about 0.01 to about 1.0 mg per kg body weight.

9. The method of claim 8, wherein $R_1$ is phosphate; $R_2$ and $R_3$ are each independently $C_{2-6}$alkenyl; and $R_4$ and $R_5$ are each independently H; or a pharmaceutically acceptable salt thereof.

10. The method of claim 8, wherein $R_2$ and $R_3$ are each independently ethenyl; or a pharmaceutically acceptable salt thereof.

11. The method of claim 8, wherein the pharmaceutically acceptable salt is a sodium salt; and/or wherein the compound is 3',5-diallyl-[1,1'-biphenyl]-2,4'-diyl bis(phosphate), or a pharmaceutically acceptable salt thereof.

12. The method of claim 8, which is sodium 3',5-diallyl-[1,1'-biphenyl]-2,4'-diyl bis(phosphate).

13. The method of claim 8, wherein the method does not cause hemorrhage.

14. The method of claim 8, wherein the method reduces edema.

15. The method of claim 8, wherein the compound has a prolonged half-life compared to honokiol.

16. The method of claim 8 wherein the compound converts to honokiol in plasma.

17. The method of claim 8, wherein the neuroprotective effect diminishes brain damage in the subject.

18. The method of claim 17, wherein the brain damage is ischemic stroke.

* * * * *